Figure 1:
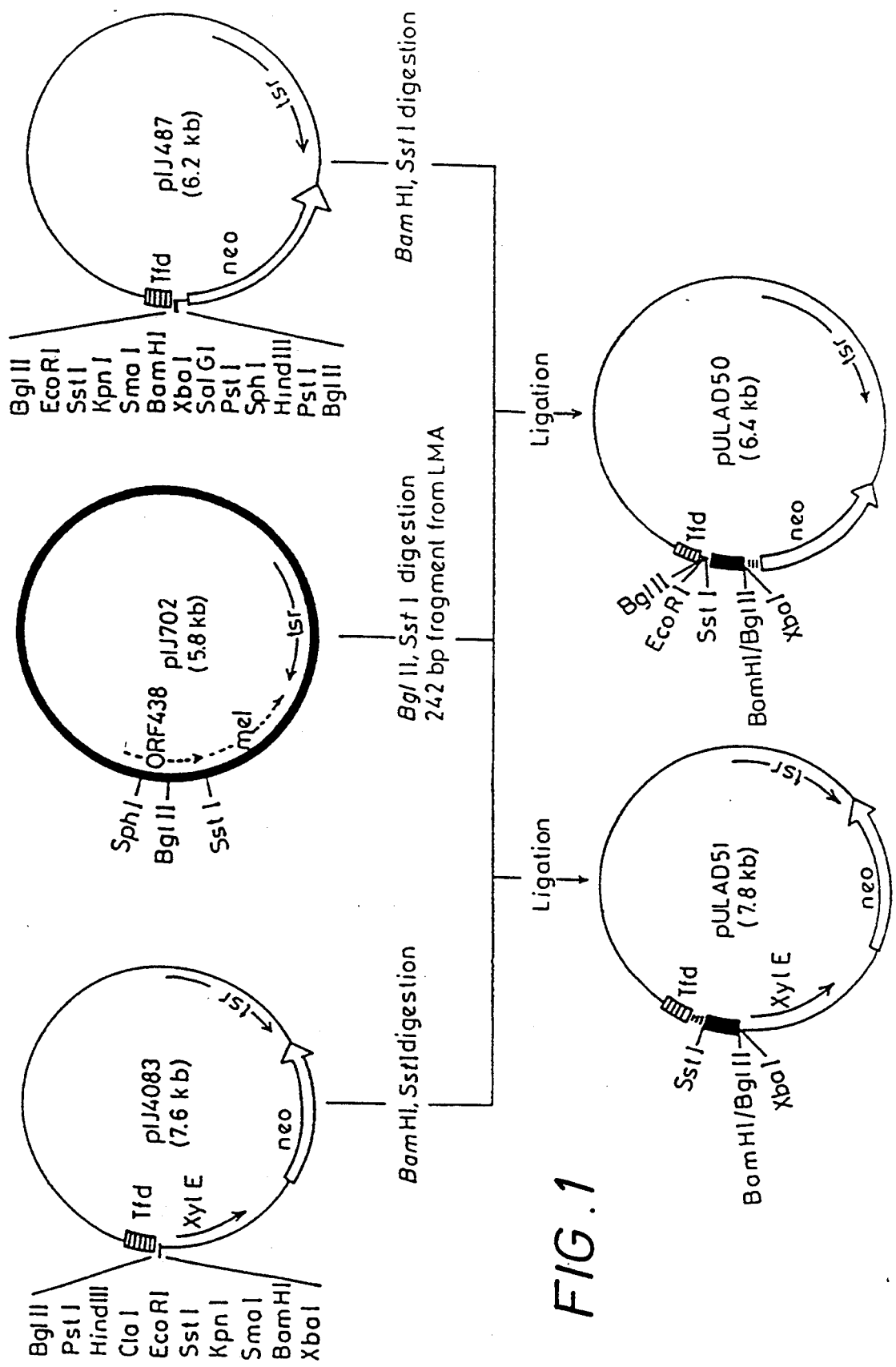

United States Patent [19]

Ortega et al.

[11] Patent Number: 5,385,841
[45] Date of Patent: Jan. 31, 1995

[54] PO438, A NEW CALCIUM-REGULATED PROMOTER

[75] Inventors: Jose D. Ortega, Sevilla; Jose A. Gil, Leon; Tomas V. Garcia, Leon; Juan F. Martin, Leon, all of Spain

[73] Assignee: Laboratorios Serono S.A., Madrid, Spain

[21] Appl. No.: 989,363

[22] Filed: Dec. 11, 1992

[30] Foreign Application Priority Data

Dec. 12, 1991 [ES] Spain .................................. 9102765

[51] Int. Cl.$^6$ ..................... C12N 15/00; C12N 1/21; C12N 15/11
[52] U.S. Cl. ............................. 435/252.35; 435/69.1; 435/320.1; 536/24.1
[58] Field of Search ............... 435/69.1, 320.1, 252.35; 536/24.1; 935/6

[56] References Cited

U.S. PATENT DOCUMENTS 4,766,066 8/1988 Kuhstoss et al. ................. 435/69.3

FOREIGN PATENT DOCUMENTS 0148552 7/1985 European Pat. Off. .
8807079 9/1988 WIPO .
9014426 11/1990 WIPO .

OTHER PUBLICATIONS

Berman et al. 1985 Gene 37:101–110.
J. M. Ward et al., "Construction and charicterisation of a series of multi-copy promoter-probe plasmid vectors for Streptomyces using the aminoglycoside phosphotransferase gene from Tn5 as indicator", Mol. Gen. Genet. (1986) 203:468–478.
M. Geistlich et al., "Localization and functional analysis of the regulated promoter from the Streptomyces glaucescens mel operon", Cell (1989) 3:1061–1069.
E. Katz et al., "Cloning and expression of the tyrosinase gene from Streptomyces antibioticus in Streptomyces limidans", J. Gen. Microbiol. (1983) 129:2703:2714.
W.-M. Leu et al., "Analysis of the promoter region of the melanin locus from Streptomyces antibioticus", Gene (1989) 84:267–277.

Primary Examiner—Richard A. Schwartz
Assistant Examiner—Gary L. Brown
Attorney, Agent, or Firm—Rothwell, Figg, Ernst & Kurz

[57] ABSTRACT

There is disclosed a new calcium-regulated promoter to be used for increasing production of extracellular enzymes, or heterologous polypeptides, a recombinant vector that includes the DNA sequence of the promoter operatively linked to a DNA encoding said enzyme or polypeptide and a host organism transformed with the recombinant vector that includes the promoter operatively linked to the DNA encoding said enzyme or polypeptide. The present invention further relates to Streptomyces expression systems and methods for expressing foreign DNA sequences in Streptomyces and for secreting to the surrounding medium polypeptides and proteins coded for by those foreign DNA sequences.

10 Claims, 6 Drawing Sheets

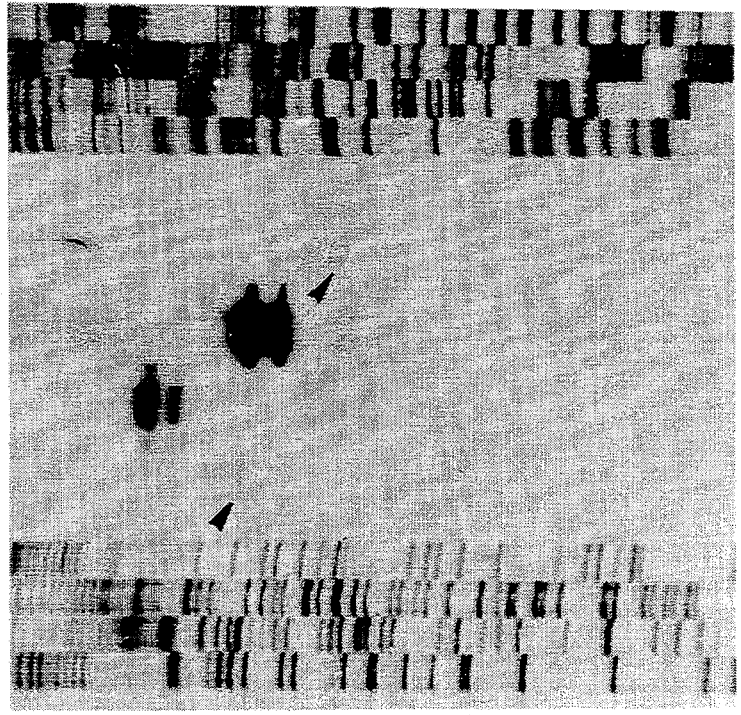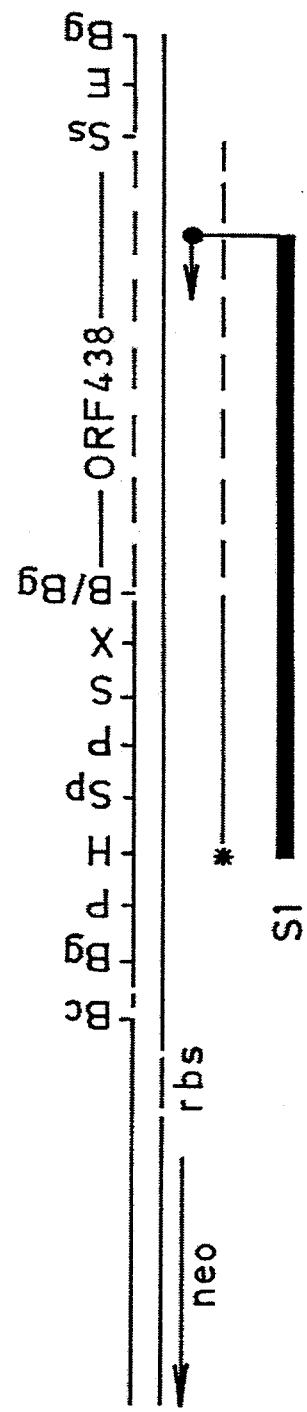
FIG. 3

FIG. 4A

```
TCGGGCCAACCGGTCCGGGCCGATTTCTCCCCTTCTCCGGTCGATAGGTATGCGGGTCGTCAACCCA
AGCGCCGGTTGGCCAGGCCCGGGCTAAAGAGGGAAGAGGAGGCCAGCTATCCATACGCCCAGCAGTTGGGT
       rbs           M  P  E  L  T  R  R  R  A  L  G  A  A  A  V  V  A
ACGCACCCCAGGAGGTCCCGCATGCCCGGAACTCACCCGTCGCCGAGCCGTCTCCCGGCGCCAGCCGTCTCGCC
TGCGTGGGTCCTCCAGGGCTACGGGTGGGCAGCGGGCGGCGGGCGGGCGGGCGGGCGTCGGCAGCAGGG A  G  V  P  L  V  A  L  P  A  A  R  A  D  D  D  R  G  H  H  T  P  E  V  P
GCCGGTGTCCCCGCTGGTCGCCCTTCCCGCCGCCCGCGCCGACGATCGGGGCCACCACCCCCGAGGTCCCC
CGGCCACAGGGCGACCAGCGGGAAGGGCGGCGGGCGCTAGCCCCGTGGTGGGGGCTCCAGGGG G  N  P  A  A  S  G  A  P  A  A  F  D  E  I  Y  K  G  R  R  I  Q  G  R
GGGAACCCGGCCGCCTCCGGCGCCCCGGCCGCCTTCGACGAGATCTACAAGGGCCGCCGGATACAGGGCCGG
CCCTTGGGCCGGCGGAGGCCGCGGGGCCGGCGGAAGCTGCTCTAGATGTTCCCGGCGGCTATGTCCCGGCC
                                                    BglII
```

FIG. 4B

```
T  V  T  D  G  G  G  H  H  G  G  G  H  G  G  G  D  G  H  G  G  G  H  H  G
ACGGTCACCGACGGCGGGGGCCACCACGGCGGGCGGTCACGGCGGTGACGGCGGTCATCACGGC
TGCCAGTGGCTGCCGCCCCGGTGGTGCCGCCCAGTGCCGCCACTGCCGCCAGTAGTGCCGCCAGTCG

G  G  Y  A  V  F  V  D  G  V  E  L  H  V  M  R  N  A  D  G  S  T  I  S
GGCGGTTACGCCGTGTTCGTTGACGGCGTCGAACTGCATGTGATGCGCAACGCCGATGGCTCGACTATCAGC
CCGCCAATGCGGCACAAGCAACTGCCGCAGCTTGACGTACACTACGCGTTGCGGCTACCGAGCACCTAGTCG

V  V  S  H  Y  E  P  V  D  T  P  R  A  A  A  R  A  A  V  D  E  L  Q  G
GTCGTCAGCCACTACGAGCCGGTGGACACCCCGCGCGCGGCGCGTGCGGCGGTCGACGAGCTCCAGGGC
CAGCAGTCGGTGATGCTCGGCCACCTGTGGGGCGCGCGCCGCGCACGCCGCCAGCTGCTCGAGGTCCCG
                                                              SstI
                                                       ←—oo

A  R  L  L  P  F  F  P  S  N  .                          M   T
GCCCGGCTCCTGCCCTTCCCCTTCCAACTGACCTTCTCCCCGCACTTTTGGAGCACCCGCACATGACC...
CGGGCCGAGGACGGGAAGGGGAAGGTTGACTGGAAGAGGGGCGTGAAAACCTCGTGGGCGTGTACTGG...
                                    rbs
```

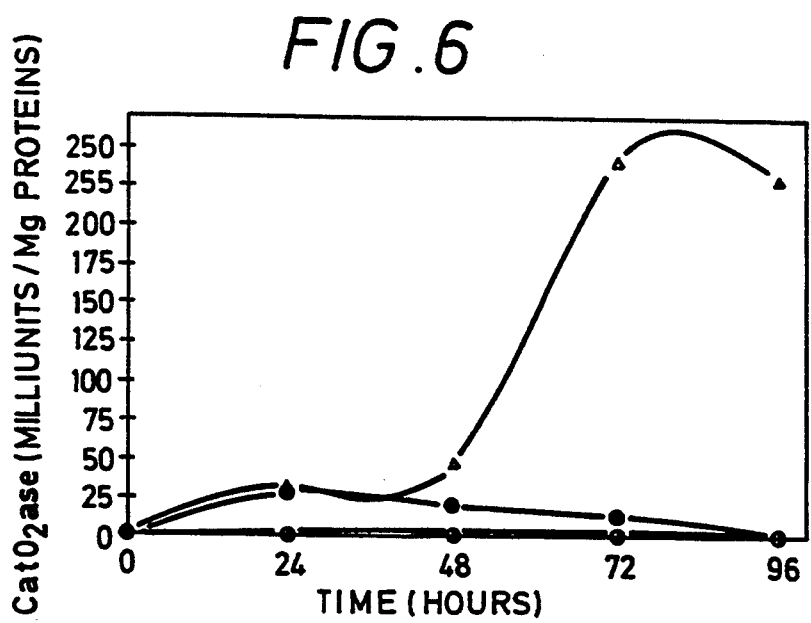

SEQUENCE LISTING ( 1 ) GENERAL INFORMATION:

( i i i ) NUMBER OF SEQUENCES: 3

( 2 ) INFORMATION FOR SEQ ID NO:1:

( i ) SEQUENCE CHARACTERISTICS:
        ( A ) LENGTH: 572 base pairs
        ( B ) TYPE: nucleic acid
        ( C ) STRANDEDNESS: both
        ( D ) TOPOLOGY: linear ( i i ) MOLECULE TYPE: DNA (genomic)

( i i i ) HYPOTHETICAL: NO ( i v ) ANTI-SENSE: NO ( i x ) FEATURE:
        ( A ) NAME/KEY: CDS
        ( B ) LOCATION: 94..531

-continued ( x i ) SEQUENCE DESCRIPTION: SEQ ID NO:1:

```
TCGCGGCCAA CCGGTCCGGG CCGATTTCTC CCCTTCTCCT CCGGTCGATA GGTATGCGGG        60

GTCGTCAACC CAACGCACCC CAGGAGGTCC CGC ATG CCG GAA CTC ACC CGT CGT      114
                                      Met Pro Glu Leu Thr Arg Arg
                                       1               5

CGC GCG CTC GGC GCC GCA GCC GTC GTC GCC GCC GGT GTC CCG CTG GTC        162
Arg Ala Leu Gly Ala Ala Ala Val Val Ala Ala Gly Val Pro Leu Val
         10              15              20

GCC CTT CCC GCC GCC CGC GCG GAC GAT CGG GGG CAC CAC ACC CCC GAG        210
Ala Leu Pro Ala Ala Arg Ala Asp Asp Arg Gly His His Thr Pro Glu
     25              30              35

GTC CCC GGG AAC CCG GCC GCG TCC GGC GCC CCC GCC GCC TTC GAC GAG        258
Val Pro Gly Asn Pro Ala Ala Ser Gly Ala Pro Ala Ala Phe Asp Glu
 40              45              50              55

ATC TAC AAG GGC CGC CGG ATA CAG GGC CGG ACG GTC ACC GAC GGC GGG        306
Ile Tyr Lys Gly Arg Arg Ile Gln Gly Arg Thr Val Thr Asp Gly Gly
             60              65              70

GGC CAC CAC GGC GGC GGT CAC GGC GGT GAC GGT CAC GGC GGC GGC CAT        354
Gly His His Gly Gly Gly His Gly Gly Asp Gly His Gly Gly Gly His
             75              80              85

CAC GGC GGC GGT TAC GCC GTG TTC GTG GAC GGC GTC GAA CTG CAT GTG        402
His Gly Gly Gly Tyr Ala Val Phe Val Asp Gly Val Glu Leu His Val
         90              95              100

ATG CGC AAC GCC GAC GGC TCG TGG ATC AGC GTC GTC AGC CAC TAC GAG        450
Met Arg Asn Ala Asp Gly Ser Trp Ile Ser Val Val Ser His Tyr Glu
     105             110             115

CCG GTG GAC ACC CCG CGC GCC GCG GCC CGC GCT GCG GTC GAC GAG CTC        498
Pro Val Asp Thr Pro Arg Ala Ala Ala Arg Ala Ala Val Asp Glu Leu
120             125             130             135

CAG GGC GCC CGG CTC CTC CCC TTC CCC TCC AAC TGACCTTCTC CCCCGCACTT      551
Gln Gly Ala Arg Leu Leu Pro Phe Pro Ser Asn
             140             145

TTGGAGCACC CGCACATGAC C                                                572
```

( 2 ) INFORMATION FOR SEQ ID NO:2:

( i ) SEQUENCE CHARACTERISTICS:
        ( A ) LENGTH: 146 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Met Pro Glu Leu Thr Arg Arg Arg Ala Leu Gly Ala Ala Ala Val Val
 1               5                  10                  15

Ala Ala Gly Val Pro Leu Val Ala Leu Pro Ala Ala Arg Ala Asp Asp
             20                  25                  30

Arg Gly His His Thr Pro Glu Val Pro Gly Asn Pro Ala Ala Ser Gly
             35                  40                  45

Ala Pro Ala Ala Phe Asp Glu Ile Tyr Lys Gly Arg Arg Ile Gln Gly
         50                  55                  60

Arg Thr Val Thr Asp Gly Gly Gly His His Gly Gly Gly His Gly Gly
 65                  70                  75                  80

Asp Gly His Gly Gly Gly His His Gly Gly Gly Tyr Ala Val Phe Val
                 85                  90                  95

Asp Gly Val Glu Leu His Val Met Arg Asn Ala Asp Gly Ser Trp Ile
             100                 105                 110

Ser Val Val Ser His Tyr Glu Pro Val Asp Thr Pro Arg Ala Ala Ala
             115                 120                 125
```

```
Arg Ala Ala Val Asp Glu Leu Gln Gly Ala Arg Leu Leu Pro Phe Pro
    130                 135                 140
Ser Asn
145
```

(2) INFORMATION FOR SEQ ID NO:3:

(i) SEQUENCE CHARACTERISTICS:
        (A) LENGTH: 219 base pairs
        (B) TYPE: nucleic acid
        (C) STRANDEDNESS: both
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:3:

```
CCGCGGCGCG CGGGGTGTCC ACCGGCTCGT AGTGGCTGAC GACGCTGATC CACGAGCCGT      60

CGGCGTTGCG CATCACATCG AGTTCGACGC CGTCCACGAA CACGGCGTAA CCGCCGCCGT     120

GATGGCCGCC GCCGTGAGCG TGACCGCCGT GACCGCCGCC GTGGTGGCCC CCGCCGTCGG     180

TGACCGTCCG GCCCTGTATC CGGCGGCCCT TGTAGATCT                            219
```

PO438, A NEW CALCIUM-REGULATED PROMOTER

The invention is in the field of biotechnology. More particularly, it relates to a new calcium-regulated promoter to be used for increasing production of extracellular enzymes, or heterologous polypeptides, a recombinant vector that includes the DNA sequence of the promoter operatively linked to a DNA encoding said enzyme or polypeptide and a host organism transformed with the recombinant vector that includes the promoter operatively linked to the DNA encoding said enzyme or polypeptide. The present invention further relates to Streptomyces expression systems and methods for expressing foreign DNA sequences in Streptomyces and for secreting to the surrounding medium polypeptides and proteins coded for by those foreign DNA sequences.

The Streptomyces are well known producers of a variety of extracellular enzymes including proteases, phosphatases, xylanases, cellulases, amylases, lipases and nucleases.

In addition, members of the genus Streptomyces produce a large number of antibiotics, pigments and other secondary metabolites and have a complex pattern of differentiation resulting in the formation of spores. In batch cultures of Streptomyces there is usually a coincidence in the production of extracellular enzymes and the onset of antibiotic production and pigment biosynthesis and sporulation. All of these processes are repressed by nutritional conditions favoring high growth rates and are derepressed by starvation of P, C or N sources. It is unlikely that enzyme secretion, formation of secondary metabolites and differentiation are completely independent but respond to similar triggering mechanisms.

Several genes of Streptomyces encoding extracellular enzymes have been cloned. These include agarase from *Streptomyces coelicolor*, endoglycosidase H from *Streptomyces plicatus*, xylanase from *Streptomyces lividans*, alpha-amylase from *Streptomyces hygroscopicus*, cellulase from Strep. spA2, beta-galactosidase from *Strep. lividans* and beta-lactamases from *Strep. cacaoi, badius* and *fradiae*.

However, the regulatory mechanisms which control expression of these genes are virtually unknown. In addition to specific regulatory mechanisms, such as induction of amylase by dextrins or maltotriose and carbon metabolite regulation of amylase or agarase, general mechanisms of derepression of several extracellular enzymes are likely to occur since simultaneous production of several polymeric-substrate degrading enzymes has been observed in Streptomyces following a nutritional down-shift. Such transacting regulatory genes have been found in *Bacillus subtilis* (J. BACTERIOL. 169:324–333, 1987), *Bacillus natto* (J. BACTEROL. 166:20–28, 1986), and *Bacillus licheniformis*.

Positive regulatory genes affecting enzyme synthesis and/or secretion can be cloned by searching for increased secretion of extracellular enzymes in a poor secretory strain such as *S. lividans*.

Systems for expressing foreign DNA sequences in Streptomyces have previously been described in, for example, EP 148,552 and WO 88/07079. These systems use the endogenous promoters of extracellular enzymes produced by Streptomyces.

The substitution of the endogenous promoters with foreign promoters has been disclosed in WO 90/14426 which describes the cloning and characterization of a newly isolated gene, the saf gene, encoding a new polypeptide, referred to as saf polypeptide, which modulates directly, or indirectly, expression of the genes for extracellular enzymes in Streptomyces by interacting with the control region of the structural genes for the extracellular enzymes.

The promoter of the saf gene has been found to be more potent than natural promoter of extracellular enzymes. For example, the amylase gene expresses much greater quantities of amylase when the saf promoter is substituted with the natural amylase promoter. Thus, the saf promoter can be used to enhance the expression of any endogenous polypeptide or protein in place of that protein's natural promoter.

For the cloning and characterization of the saf gene, plasmid pIJ702 (Katz et al., J. GEN. MICROBIOL. 129:2703–2714, 1983) was used as a cloning vector. This plasmid contains the gene of tyrosinase, the enzyme responsible for the formation of melamin from tryosine in several species of Streptomyces. The mel locus in pIJ702 has been sequenced and two open reading frames (ORFs) have been identified: the first is the ORF corresponding to the mel gene that codes for the polypeptide chain of tyrosinase, the second ORF, located upstream of the mel gene, was named ORF438 (Bernan et al., GENE 37:101–110, 1985) and its role is yet unclear.

During the study carried out to locate precisely the saf gene, fragment SstI-KpnI (432 nucleotides-saf gene without promoter) was inserted into the BglII site of pIJ702. A surprising aspect of the study was the lack of expression of this fragment when inserted with the right orientation and its expression when inserted with the opposite direction (clockwise direction) to ORF438. This finding implied the presence of a fragment with promoter activity, before the gene mel and at the BglII cloning site, located within the ORF438, with opposite orientation.

A principal object of this invention is to provide a new promoter which has been identified in a DNA fragment contained within the ORF438 of pIJ702 plasmid. The promoter activity is positively regulated by calcium ions and expression of the genes for extracellular enzymes in Streptomyces, operatively linked to said promoter, is greatly increased in the presence of $CaCl_2$ solutions.

It is another aspect of the present invention to provide cloning vehicles (vectors) which include said promoter operatively linked to an endogenous or foreign DNA sequence encoding a polypeptide or protein, as well as host organisms or cells transformed with such cloning vehicles, thereby resulting in expression and secretion of the polypeptide encoded by said DNA sequence.

Another aspect of the present invention is the integration of such a cloning vehicle carrying a foreign DNA sequence into the chromosomal DNA of Streptomyces.

It is yet another aspect of the present invention a process for the preparation of an extracellular enzyme, a desired polypeptide or protein by culturing a transformed host organism according to the present invention and recovering the product from the culture broth.

The new promoter contained in the ORF438 shows promoter activity in opposite orientation to that of the ORF438 and is hereinafter referred to as Po438 (Promoter opposite to the ORF438). The knowledge of its clockwise promoter activity in pIJ702 is very important so as to avoid erroneous interpretations in gene expression studies of DNA fragments cloned in this vector.

The Po438 promoter is the first known calcium-regulated promoter that has been characterized in Streptomyces and can be used to enhance expression in Streptomyces of selected heterologous proteins by inserting the DNA fragment containing the Po438 promoter into a suitable cleavage site upstream of the gene coding for the desired protein in a suitable cloning vehicle, transforming a Streptomyces host with such cloning vehicles and culturing the transformed bacteria in the presence of a $Ca^{2+}$ solution to excrete the selected protein or portion thereof.

The promoter activity of Po438 has been detected using two different promoter-probe vectors. The DNA fragment containing the Po438 promoter was subcloned in two different plasmids carrying the promoterless aminoglycoside phosphotransferase gene (neo) and the promoterless catechol dioxygenase gene (XylE) respectively (FIG. 1). Both genes expressed great quantities of each enzyme in the presence of increasing concentrations of calcium ions, thus indicating the calcium-regulated promoter activity of Po438.

The transcription start point in Po438 was determined through a S1 nuclease mapping experiment, which situated the start point around the C at 24 nt from the SstI site (FIG. 4).

Referring to the accompanying drawings:

FIG. 1 Construction of plasmids pULAD50 and pULAD51 carrying the 242 bp SstI-BglII fragment of pIJ702 (containing P0438) cloned in the promoter-probe vectors pIJ487 (Ward et al., 1986) and pIJ4083.

Figure 2:
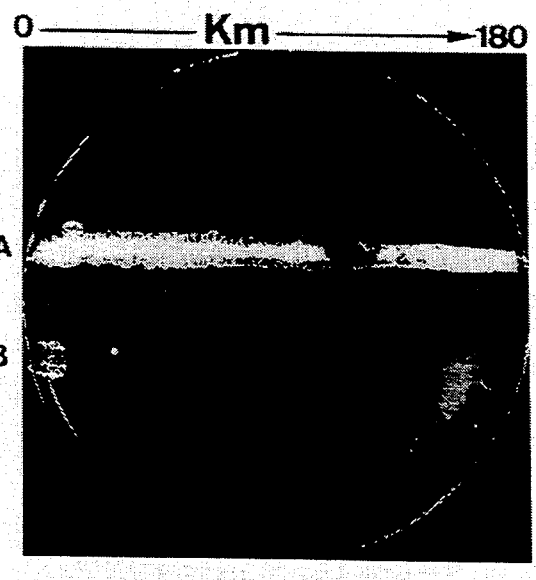

FIG. 2 Promoter activity of the 242 bp SstI-BglII fragment of pIJ702. A kanamycin gradient (o-180 ug/ml) was established on solid MM medium (Hopwood, 1967) and was streaked with S. lividans carrying the plasmid pULAD50 (A) or pIJ487 (B).

FIG. 3 Schematic representation of a region of pULAD50 carrying the 242 bp SstI-BglII fragment of pIJ702 and strategy followed for S1 mapping. In the diagram the bar marked with asterisk represents the labeled fragment, and the bar with S1 represents the protected fragment obtained. Lanes A-C-G-T show the four sequence reactions for the M13mp18 single strand DNA (right) and for the 242 bp SstI-BglII fragment from pIJ702 (left).

1-Protected fragment in the hybridization between the 270 nt HindIII-SstI fragment of pULAD50 and mRNA from S. lividans [pULAD50].

2-270 nt HindIII-SstI probe.

3-242 nt BglII-SstI probe.

4-Protected fragment in the hybridization between the 242 nt BglII-SstI fragment of pIJ702 and mRNA from S. lividans [pIJ702].

The arrowheads indicate the hybridization bands corresponding to the protected fragments.

FIG. 4 Nucleotide sequence (SEQ ID NO:1) of the DNA region in the mel cluster that contains the ORF438 indicating its amino acid sequence. The BglII and SstI restriction sites which flank the DNA fragment cloned in pIJ487 to construct pULAD50 are indicated. The two first amino acids of the tyrosinase are also shown.

●●→Initiation of the mel transcript according to Geistlich et al. (1989) and Leu et al. (1989).

∞→Transcription initiation from Po438 according to S1 nuclease mapping experiments (FIG. 3).

rbs, ribosome-binding site.

Figure 5:
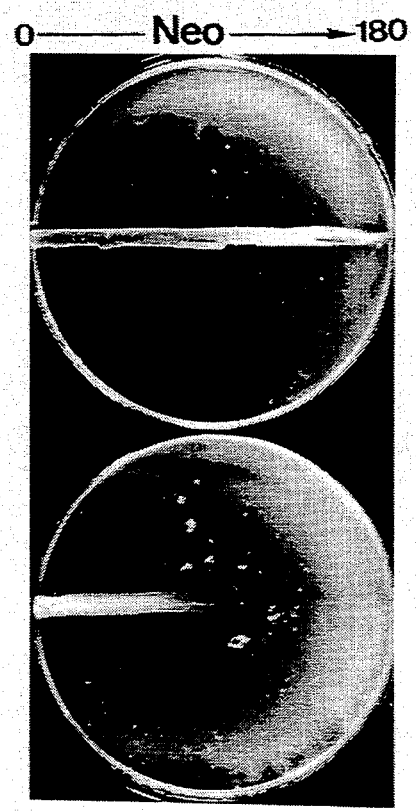

FIG. 5 Phosphate repression of expression from the Po438 promoter. A neomycin gradient (0-180 ug/ml) was made on solid MM+TES buffer 825 mM, pH 7.2) (upper plate), and on the same medium supplemented with 20 MM sodium phosphate buffer, pH 7.2 (lower plate). Both plates were streaked with a similar amount of S. lividans [pULAD50] spores.

FIG. 6 Calcium induction in Streptomyces of the promoterless XylE gene of Pseudomonas putida when placed downstream of the Po438 promoter. S. lividans [pULAD51] was grown in calcium-free R2YE liquid medium (●) and R2YE medium supplemented with additional $CaCl_2$ up to 60 mM (Δ). Catechol dioxygenase activity (Cat $O_2$ ase) of S. lividans transformed with pIJ4083 (o) was not altered when grown in R2YE medium with or without $CaCl_2$.

The work described herein was performed employing the following materials and methods.

Bacterial strains and plasmids. The Streptomyces strains and plasmids used in this study are listed in Table 1.

Media and culture conditions. Transformation of protoplasts. Streptomyces strains were grown in R2YE, minimal medium (MM) or YEME supplemented with 34% sucrose and 5 mM $MgCl_2$ (Hopwood et al., Genectic manipulation pf Streptomyces. A LABORATORY MANUAL. The John Innes Foundation, Norwich, U.K., 1985). Liquid cultures of Streptomyces were grown in triple baffled flasks at 28° C. in a rotary shaker with an agitation of 220 rpm.

Preparation and transformation of S. lividans protoplasts were as described (Thompson et.al., J. BACTERIOL. 151:668-677, 1982).

DNA isolation, manipulation and DNA sequencing. Plasmid DNA was isolated following the Kieser method (Kieser et al., PLASMID 12:19-36, 1984). Digestions and ligations were monitored by agarose gel electrophoresis. The conditions for digestion with a restriction endonuclease and ligation reactions were those recommended by the manufacturers. Subcloning of DNA fragments was carried out by digesting 1-2, ug of plasmid DNA with adequate restriction enzyme(s) and the reaction products were separated by gel electrophoresis in low melting point agarose (LMPA).

The nucleotide sequence was determined by the chain termination method of Sanger (Sanger et al., PROC. NATL. ACAD. SCI. USA 74:5463-5467, 1977) using M13 clones (Messing et al., NUCL. ACIDS RES. 9: 309-321, 1981).

RNA isolation and S1 nuclease mapping. RNA was isolated according to Kirby (Kirby et al., BIOCHEM. J. 104:258-262, 1967) from 50 hour cultures in MM medium. For S1 mapping the DNA probes were end labelled (Maxam and Gilbert, METHODS ENZYMOL. 65: 499-560, 1980). RNA (40 ug) was mixed with $10^5$ c.p.m. of [$^{32}$p]-end labelled DNA fragment and denatured at 85° C. for 15 mins. (Favalora et al., METHODS ENZYMOL. 65:718-749, 1980). Hybridization was carried out at 60° C. for 3 h, treated with 60 units of S1 nuclease and the S1 digestion product was loaded onto a 7% (w/v) polyacrylamide gel containing 7 M urea, and run in parallel with the M13 mp18 phage and the 242 bp BglII-SstI fragment of pIJ702 sequenced by the Sanger method.

Detection of catechol dioxygenase activity. For plate assays, Streptomyces transformant colonies were grown at 28° C. for 3 days and the plates were sprayed with an aqueous solution of 0.5 M catechol. For liquid assays, Streptomyces strains were grown at 28° C. 50 ml of R2YE liquid medium without $CaCl_2$ or supplemented with $CaCl_2$ (60 mM). At different times samples were taken and catechol dioxygenase activities were determined as described (Ingram et al., J. BACTERIOL. 171:6617-6624, 1989). Protein concentrations were determined by the Bradford method by using bovine serum albumine as the standard (Bradford, ANAL. BIOCHEM. 72:248-254, 1976).

The following detailed description will illustrate the invention:

Promoter activity of Po438

The promoter activity of Po438 has been determined through the expression of the aminoglycoside phosphotransferase gene and the catechol dioxygenase gene contained in two different promoter-probe vectors.

Expression of the aminoglycoside phosphotransferase gene. A 242 bp BglII-SstI fragment from pIJ702 plasmid was subcloned into pIJ487 (Ward et al., MOL. GEN. GENET. 203:468-478, 1986), which carried a promoterless aminoglycoside phosphotransferase gene (neo). Expression of this gene confers Kanamicin (km) and neomycin resistance to Streptomyces lividans. Plasmid pULAD50 was thus created (FIG. 1). S. Lividans transformed with pULAD50 was able to grow on MM containing more than 150 ug/ml of Km, whereas S. lividans transformed with pIJ487 (promoter-probe vector without inserted promoter) does not grow on MM with 10 ug/ml Km as shown in FIG. 2. This result clearly indicates that the BglII-SstI fragment of pIJ702 has promoter activity in Streptomyces, with orientation from the SstI site to the BglII site.

Expression of the catechol dioxygenase gene. The 242 bp BglII-SstI fragment as in the above example wa subcloned into a different promoter-probe vector, the plasmid pIJ4083 which carried the XylE gene from Pseudomonas putida, coding for the enzyme catechol dioxygenase. The hybrid plasmid was named pULAD51 (FIG. 1). Stremtomyces lividans transformed with pULAD51 was grown in R2YE medium supplemented with $CaCl_2$ up to 60 Mm. Quantitation of Catechol dioxygenase activity indicated that Po438 exerts promoter activity also when inserted upstream of the XylE gene (FIG. 6).

Regulation of the expression from Po438 by calcium ions

The effect of different ions on the promoter activity of Po438 has been analyzed. Since the level of Kanamycin resistance is dependent on the amount of salt in the growth medium (Hopwood et al., Genetic Manipulation of Streptomyces. A Laboratory Manual. The John Innes Foundation, Norwich, U.K. 1985), Neomycin (Neo) was used in MM for these studies. In all cases MM was supplemented with TES buffer (25 mM, pH 7.2) in order to avoid pH changes. $Mg^{2+}$, $Fe^{2+}$, $Zn^{2+}$, $Cu^{2+}$ cations had no effect on the strength of Po438 (resistance to 170 ug/ml Neo on MM plates), whereas several monovalent cations ($Na^+$, $K^+$, $Li^+$, $Cs^+$, 10 mM) exerted a weak reduction of the promoter activity and there was no growth on MM containing more than 100 ug/ml of Neo. A reduction in promoter activity was also observed when the MM was supplemented with sodium phosphate buffer (20 mM, pH 7.2) as shown in FIG. 5.

Calcium ions positively regulate the promoter activity of Po438. $Ca^{2+}$ greatly increased Neo resistance of S. lividans transformed with pULAD50 plasmid and a strict correlation between $CaCl_2$ concentration and Neo level restistance has been shown (Table 2).

Plasmid pULAD60 represents an example of a similar plasmid with the same neo-gene linked to a different promoter, the saf promoter, as has been described in WO 90/14426. The Neo resistance of S. lividans transformed with pULAD60 was not, however, modified when growing on MM containing different concentrations of $CaCl_2$(0, 10, 20, 30, 40 mM), suggesting that there is not a post-translational stimulation of the neo gene product, nor a calcium inactivation of Neomycin. If the effect of $Ca^{2+}$ were not specific, the stimulating effect should be observed with all the constructions. This demonstrates that the Po438 promoter activity is specifically regulated by calcium ions.

Calcium induction was also observed in the expression of XylE in S. lividans transformed with plasmid pULAD51 as reported in FIG. 6. Catechol dioxygenase activity (Cat $O_2$ ase) greatly increased when the R2YE culture medium was supplemented with $CaCl_2$ up to a 60 Mm concentration. Catechol dioxygenase activity of S. lividans transformed with pIJ4038 (the promoter-probe vector without the Po438 promoter) was, on the contrary, not altered when grown in R2YE medium with or without calcium chloride.

Determination of the transcription start point in Po438

S1 nuclease mapping experiments were carried out to determine the transcription start point and the sequence of the Po438 promoter. A 270 bp HindIII-SstI fragment isolated from pULAD50 was labelled in the HindIII 5' end and hybridized with mRNA isolated from S. lividans carrying pULAD50. The protected fragment showed in a size of around 24 nt shorter than the control probe (FIG. 3) what situated the transcription start point around the C at 24 nt from the SstI site (FIG. 4). A second S1 nuclease mapping experiment was performed with the original plasmid pIJ702, which also contains the Po438 DNA region. The 242 bp BglII-SstI fragment of pIJ702 was used as a probe. The fragment was labelled in the BglII 5' end and hybridized with mRNA isolated from S. lividans transformed with pIJ702. FIG. 3 shows that the protected fragment was still 24 nt shorter than the probe, indicating that the transcription initiation occurs in pIJ702 in a similar nucleotide as in pULAD50.

FIG. 4 shows the promoter region of the mel gene in ORF 438, located about 30 nt upstream from the start codon of the ORF 438 (Geistlich et. al., Molecular Microbiology 3: 1061-1069, 1989; Leu et al., GENE 84:267-277, 1989) as well as the Po438 promoter located in opposite orientation to that of ORF 438 and its transcription start point according to the S1 nuclease mapping experiments of this work.

While the aminoglycoside phosphtransferase gene and the catechol dioxygenase gene have been specifically exemplified, it should be understood that for the purpose of enhancing expression through the use of the Po438 promoter, the gene for any polypeptide or protein produced by the Streptomyces species being used can be modified by removing the native promoter and substituting the Po438 promoter. Similarly, the foreign DNA coding for a polypeptide or protein can be inserted into any such endogenous gene. Preferably, however, the endogenous gene selected will be one which expresses the protein through the cell wall and into the culture medium, in which case, it is important to retain the secretion signal sequence. The foreign DNA is thus preferably inserted in such a way as to retain the secretion signals as much as possible from the extracellular enzyme gene. While these signals are predominantly on the leader sequence, there is evidence with respect to endogenous genes for extracellular enzymes that the terminal carboxyl end is also important for secretion. Thus, it may be best to create a fusion protein by inserting the foreign DNA into the endogenous DNA, rather than removing the transcriptional part of the endogenous DNA and substituting the foreign DNA.

It should also be understood that the foreign DNA sequence may be any non-Streptomyces-derived DNA sequence encoding a protein or polypeptide, particularly one of eukaryotic or viral origin. Examples of such eukaryotic and viral DNA sequences are sequences encoding human and animal leukocyte interferons (IFN-alpha), fibroblast interferons (IFN-beta), and immune interferons (IFN-gamma), human insulin, human and animal growth and other hormones, such as corticotropin releasing factor (CRF), human serum albumin and various human blood factors and plasmignogen activators, both tissue and urokinase, hepatitis B viral core and surface antigens, FMD viral antigens and other human, animal and viral polypeptides and proteins.

TABLE 1

| Strains and plasmids | | |
|---|---|---|
| Designation | Relevant characteristics | Source of reference |
| S. lividans JI1326 | wild type | JI |
| S. antibioticus ATCC 11891 | wild type, melanin producer | ATCC |
| pIJ702 | thiostrepton resistance and melanin+ | Katz et al. 1983 |
| pULAD60 | PIJ702 carrying the saf promoter | WO 90/14426 |
| pIJ487 | promoter-probe vector for Strentomyces carrying the neo gene as reporter | Ward et. al. 1986 |
| pULAD60 | pIJ487 carrying the 242 bp SstI-BqlII fragment from pIJ702 | This work |
| pIJ4083 | promoter-probe vector for | |

TABLE 1-continued

| Strains and plasmids | | |
|---|---|---|
| Designation | Relevant characteristics | Source of reference |
| pULAD51 | Streptomyces carrying the XylE gene as reporter pIJ4083 carrying the 242 bp SstI-BalII fragment from pIJ702 | This work |

JI, Collection of microorganisms of the John Innes Institute, Colney Lane, Norwich; NR4UH, UK; ATCC, American Type Culture Collection

TABLE 2

| Level of neomycin resistance of S. lividans [pULAD50] growing on solid MM supplemented with CaCl₂ | |
|---|---|
| CaCl₂ concentration (mM) | Neo resistance (μg/ml) |
| 0 | 180 |
| 10 | 300 |
| 20 | 650 |
| 30 | 1100 |
| 40 | 1900 |

References Quoted in the Figures and Table 1

GEISTLICH M., Irniger S. and Hutter R.: Localization and functional analysis of the regulated promoter from the Streptomyces glaucescens mel operon. Molecular Microbiology. 3 (1989) 1061–1069.

HOPWOOD. D. A.: Genetic analysis and genome structure in *Streptomyces coelicolor.* Bacterial. Rev. 31 (1967) 373–403.

KATZ, E., Thompson, C. J. and Hopwood, D. A.: Cloning and expression of the tyrosinase gene from *Streptomyces antibioticus* in *Streptomyces lividans.* J. Gen. Microbiol. 129 (1983) 2703–2714.

LEU, W. -M., Wu, S. -Y., Lin, J. -J., Lo, S. J. and Wu Lee, Y. -H.: Analysis of the promoter region of the melanin locus from *Streptomyces antibioticus.* Gene 84.(1989) 267–277.

WARD, J. M., Janssen, G. R., Kieser, T., Bibb, M. J., Buttner, M. J. and Bibb, M. J.: Construction and characterization of a series of multi-copy promoter-probe plasmid vectors for Streptomyces using the aminoglycoside phosphotransferase gene from Tn5 as indicator, Mol. Gen. Genet. 203 (1986) 468–478.

We claim:

1. A DNA fragment comprising the calcium-regulated promoter contained in FIG. 4 (SEQ ID NO:1) or a fragment thereof having calcium regulated promoter activity.

2. A DNA fragment comprising the calcium-regulated promoter contained in SEQ ID NO:1 which is oriented in a direction opposite to the reading frame of ORF438.

3. The DNA fragment of claim 1 wherein said promoter is a double-stranded DNA fragment.

4. The DNA fragment of claim 3 wherein the calcium-regulated promoter is the BglIII-Sst I fragment of FIG. 4 (SEQ ID NO:1).

5. A cloning vehicle comprising a DNA sequence encoding a polypeptide or protein operatively linked to a DNA fragment in accordance with claim 1.

6. A cloning vehicle in accordance with claim 5, wherein said DNA sequence is one which is endogenous to Streptomyces.

7. A cloning vehicle in accordance with claim 5, wherein said DNA sequence comprises all or part of a sequence encoding a polypeptide or protein endogenous to Streptomyces to which has been fused, in the same reading frame, a DNA sequence encoding a non-Streptomyces polypeptide or protein.

8. A Streptomyces host cell transformed with a cloning vehicle in accordance with claim 5.

9. A Streptomyces host cell transformed with a cloning vehicle in accordance with claim 6.

10. A Streptomyces host cell transformed with a cloning vehicle in accordance with claim 7.

* * * * *

UNITED STATES PATENT AND TRADEMARK OFFICE
CERTIFICATE OF CORRECTION

PATENT NO. : 5,385,841
DATED : January 31, 1995
INVENTOR(S) : A.D. Ortega et al.

It is certified that error appears in the above-indentified patent and that said Letters Patent is hereby corrected as shown below:

On the title page: Item [75]

first inventor's name should be replaced with -- Antonio D. Ortega --;
Col. 5, before and after line 16, insert a space and center line 16 as a subheader; Col. 5, line 38, "wa" should be -- was --; Col. 5, before and after lines 49-50, insert a space and center lines 49-50 as a subheader; Col. 6, line 23, "CaCl$_2$up" should be -- CaCl$_2$ up --; Col. 6, before and after lines 29-30, insert a space and center lines 29-30 as a subheader; Col. 7, in TABLE 1, under "Designation" subheading, the sixth entry, "pULAD60" should be -- pULAD50 --;
In the Claims: Col. 11, line 36 (claim 1), "FIG. 4(SEQ ID NO:1)" should be -- FIG. 4 (SEQ ID NO:1) --; Col. 11, line 37 (claim 1), "calcium regulated" should be -- calcium-regulated --.

Signed and Sealed this

Twenty-ninth Day of August, 1995

*Attest:*

BRUCE LEHMAN

*Attesting Officer*  *Commissioner of Patents and Trademarks*